US009227942B2

(12) United States Patent
Yoshizawa et al.

(10) Patent No.: US 9,227,942 B2
(45) Date of Patent: Jan. 5, 2016

(54) METHOD FOR PRODUCING 5-(DIFLUOROMETHYL)PYRAZINE-2-CARBOXYLIC ACID AND PRODUCTION INTERMEDIATE THEREOF

(71) Applicant: Eisai R&D Management Co., Ltd., Tokyo (JP)

(72) Inventors: Kazuhiro Yoshizawa, Kamisu (JP); Masayuki Omori, Kamisu (JP); Yuzo Watanabe, Kamisu (JP); Mitsuo Nagai, Tsukuba (JP); Masabumi Takahashi, Kamisu (JP); Francis G. Fang, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/396,261

(22) PCT Filed: Apr. 25, 2013

(86) PCT No.: PCT/JP2013/062863
§ 371 (c)(1),
(2) Date: Oct. 22, 2014

(87) PCT Pub. No.: WO2013/162065
PCT Pub. Date: Oct. 31, 2013

(65) Prior Publication Data
US 2015/0087836 A1 Mar. 26, 2015

Related U.S. Application Data

(60) Provisional application No. 61/639,362, filed on Apr. 27, 2012.

(51) Int. Cl.
C07D 241/24 (2006.01)
(52) U.S. Cl.
CPC .................................... C07D 241/24 (2013.01)
(58) Field of Classification Search
CPC ...................................................... C07D 241/24
See application file for complete search history.

(56) References Cited

U.S. PATENT DOCUMENTS

2009/0209755 A1 8/2009 Suzuki et al.
2010/0093999 A1 4/2010 Motoki et al.

FOREIGN PATENT DOCUMENTS

| EP | 2233474 | 9/2010 |
| JP | 4520533 | 5/2010 |
| JP | 2011-105657 | 6/2011 |
| JP | 2012-167047 | 9/2012 |
| WO | 2007/087129 | 8/2007 |
| WO | 2009/091016 | 7/2009 |
| WO | 2010/009155 | 1/2010 |
| WO | 2010/038686 | 4/2010 |
| WO | 2011/005738 | 1/2011 |
| WO | 2011/009897 | 1/2011 |
| WO | 2011/009898 | 1/2011 |
| WO | 2011/138293 | 11/2011 |

OTHER PUBLICATIONS

Ashwood et al, "Copper-mediated reaction of 2-halopyridines with ethyl bromodifluoroacetate", Tetrahedron Lett., 43 (2002) 9271.
Burton and Easdon, "The α, α-Difluoro Reformatsky Reagent: Pregeneration and Structural Determination", J. Fluorine Chem., 1988, 38, 125.
Forman et al., "Differential Effects of the Swedish Mutant Amyloid Precursor Protein on β-Amyloid Accumulation and Secretion in Neurons and Nonneuronal Cells", , The Journal of Biological Chemistry, Dec. 19, 1997, 272 (51), pp. 32247 to 32253.
Fujikawa et al., "A New Method for Aromatic Difluoromethylation: Copper-Catalyzed Cross-Coupling and Decarboxylation Sequence from Aryl Iodides", Org. Lett., 13 (2011) 5560.
Glenner and Wong, "Alzheimer's Disease: Initial Report of the Purification and Characterization of a Novel Cerebrovascular Amyloid Protein", Biochemical and biophysical research communications, May 16, 1984, 120 (3), pp. 885 to 890.
Gong et al., "Alzheimer's disease-affected brain: Presence of oligomeric Aβ ligands (ADDLs) suggests a molecular basis for reversible memory loss", Proceeding National Academy of Science USA Sep. 2, 2003; 100 (18), pp. 10417 to 10422.
Gouras et al., "Intraneuronal Aβ42 Accumulation in Human Brain", American Journal of Pathology, Jan. 2000 156 (1), pp. 15 to 20.
Hannick, and Kishi., "Improved Procedure for the Blaise Reaction: A Short, Practical Route to the Key Intermediates of the Saxitoxin Synthesis", J. Org. chem., 48, 3833 (1983).
Hock et al., "Antibodies against β-Amyloid slow Cognitive Decline in Alzheimer's Disease", Neuron, May 22, 2003; 38, pp. 547 to 554.
International Search Report for PCT/JP2013/062863 dated Jun. 11, 2013.
Jarrett et al., "The Carboxy Terminus of the β Amyloid Protein Is Critical for the Seeding of Amyloid Formation: Implications for the Pathogenesis of Alzheimer's Disease", Biochemistry, 1993, 32 (18), pp. 4693 to 4697.
Kirk, K. L., "Fluorination in Medicinal Chemistry: Methods, Strategies, and Recent Developments", Org. Process Res. Dev. (2008), 12, 305.
Konas et al., "The Synthesis of (2S)-4,4-Difluoroglutamyl γ-Peptides Based on Garner's Aldehyde and Fluoro-Reformatsky Chemistry", J. J. Pankuch, J. K. Coward, Synthesis, 2002, 2616.
Masters et al., "Amyloid plaque core protein in Alzheimer disease and Down syndrome", PNAS, USA, Jun. 1985, 82 (12), pp. 4245 to 4249.

(Continued)

Primary Examiner — Brian McDowell
(74) Attorney, Agent, or Firm — Fish & Richardson P.C.

(57) ABSTRACT 5-(Difluoromethyl)pyrazine-2-carboxylic acid, which is a raw material for the construction of 5-(difluoromethyl)pyrazine-2-carboxamide, which is a common partial structural motif of the compound having an Aβ production inhibitory action or a BACE1 inhibitory action, can be industrially advantageously produced by decarboxylating 5-[carboxy(difluoro)methyl]pyrazine-2-carboxylic acid, which is obtainable from 5-chloropyrazine-2-carboxylate.

1 Claim, No Drawings

(56) References Cited

OTHER PUBLICATIONS

Pan et al., "Novel α,α-Difluorohomophthalmides via Copper-Catalyzed Tandom Cross-Coupling-Cyclization of 2-Halobenzamides with α-α-Difluoro Reformatskii Reagent", C. P. Holmes, D. Tumelty, J. Org. Chem., 2005, 4897.

Reformatsky, S,"neue Synthese Zweiatomiger einbasischer Sauren aus den Ketonen". Ber., 20, 1210 (1887).

Sato et al., "Reactions of ethyl bromodifluoroacetate in the presence of copper powder", Kumadaki et al., J. Fluorine Chem., 125 (2004) 509.

Scheuner et al., "Secreted amyloid β-protein similar to that in the senile plaques of Alzheimer's disease is increased in vivo by the presenilin 1 and 2 and *APP* mutations linked to familial Alzheimer's disease", Nature Medicine, Aug. 1996, 2 (8), pp. 864 to 870.

Schlosser, M. and Cottet, F., "Silyl-Mediated Halogen/Halogen Displacement in Pyridines and Other Heterocytes", Eur. J. Org. Chem., 2002, 4181.

Singh and Shreeve, "Recent Advances in Nucleophilic Fluorination Reactions of Organic Compounds Using Deoxofluor and DAST", Synthesis (2002) 2561.

Taguchi et al., "Synthesis of 2,2-Difluoroesters by iododifluoroacetate-copper with organic halides", Tetrahedron Lett., 27 (1986) 6103.

Tanaka et al.,"Reformatsky and Luche Reaction in the Absence of Solvent", J. Org. Chem., 56, 4333 (1991).

Yajima and Munakata, "Synthesis of 2- and 4-Bromoquinolines", Chem. Left., 1977, 891.

Extended European Search Report in EP App. No. 13781634.4, Aug. 11, 2015, 8 pages.

Office Action for corresponding CN Patent Application No. 201380021262.X, dated Sep. 8, 2015 (with English Translation).

Yu et al., "Novel Synthesis of 1,2-Diaryl-2,2-Difluoroethanones", Tetrahedron Letter, 35(48):8955-8956 (1994).

METHOD FOR PRODUCING 5-(DIFLUOROMETHYL)PYRAZINE-2-CARBOXYLIC ACID AND PRODUCTION INTERMEDIATE THEREOF

CROSS REFERENCE TO RELATED APPLICATIONS

This application is a national phase filing under 35 U.S.C. §371 of International application number PCT/JP2013/062863, filed Apr. 25, 2013, which claims priority from provisional application No. 61/639,362 filed Apr. 27, 2012.

TECHNICAL FIELD

The present invention relates to a method for producing 5-(difluoromethyl)pyrazine-2-carboxylic acid, which is an important intermediate for the synthesis of a compound useful for obtaining the amyloid β production-inhibitory action or as an inhibitor of a beta-site amyloid precursor protein (hereinbelow, referred to as APP) cleaving enzyme, and a production intermediate thereof.

BACKGROUND ART

Alzheimer's disease is a disease characterized by senile plaque formation and neurofibrillary tangles associated with nerve cell degeneration and nerve cell loss. At present, treatment of Alzheimer's disease is limited to symptomatic treatment with symptom-ameliorating agents represented by an acetylcholinesterase inhibitor, and no radical therapeutic agent for suppression of disease progression has been developed. Development of a method for controlling the etiology of the pathological condition is necessary for creation of a radical therapeutic agent for Alzheimer's disease.

The Amyloid β (hereinbelow, referred to as Aβ) protein, which is a metabolite of APP, is assumed to be largely associated with nerve cell degeneration and nerve cell loss, and further, the expression of symptoms of dementia (see, for example, Non Patent Literatures 1 and 2). The Aβ protein is mainly composed of Aβ40, which is composed of 40 amino acids, and Aβ42, which is composed of the 40 amino acids plus two additional amino acids at the C-terminus. The Aβ40 and Aβ42 are highly likely to aggregate (see, for example, Non Patent Literature 3), and are the main components of senile plaques (see, for example, Non Patent Literatures 3, 4, and 5). Moreover, mutation in the APP and presenilin genes observed in familial Alzheimer's disease is known to increase the Aβ40 and Aβ42 (see, for example, Non Patent Literatures 6, 7, and 8). Accordingly, a compound capable of reducing the production of Aβ40 and Aβ42 is expected to serve as an inhibitor or preventive drug for the progression of Alzheimer's disease.

Aβ is produced by cleavage of APP by a beta-site amyloid β precursor protein cleaving enzyme 1 (hereinbelow, referred to as BACE1 or beta-secretase), followed by further cleavage by gamma-secretase. In light of the above, with an aim to inhibit the production of Aβ, creation of a gamma-secretase inhibitor and a beta-secretase inhibitor has been attempted. Condensed ring compounds having a beta-secretase inhibitory action have been reported in literatures such as Patent Literatures 1 to 9 shown below, and especially, Patent Literatures 1 to 6 describe condensed aminodihydrothiazine derivatives and compounds having a BACE1 inhibitory activity.

The aforementioned Patent Literatures 1 to 5 and 7 to 8 describe a number of amide compounds represented by the following formulae, which are important compounds in the production of pharmaceutical products.

[Formula 1]

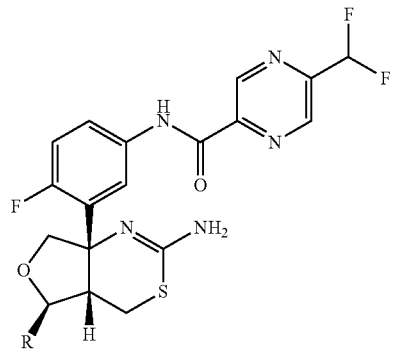

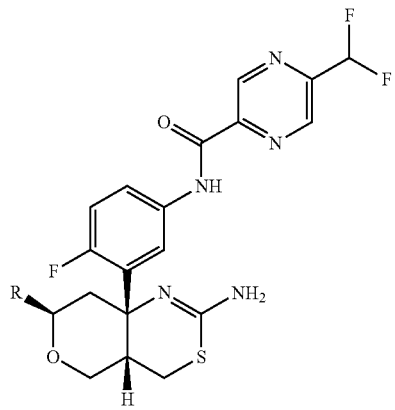

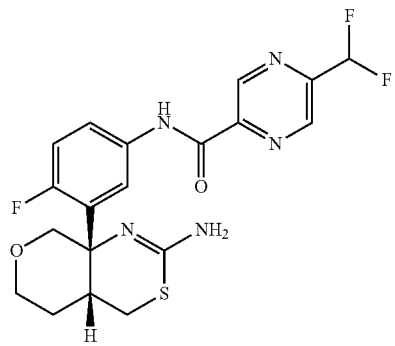

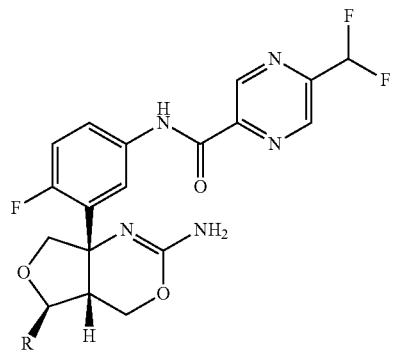

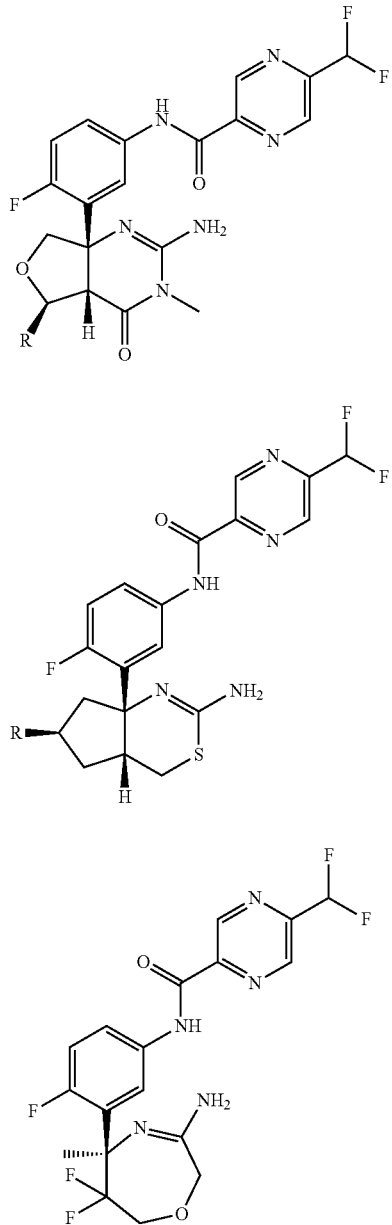

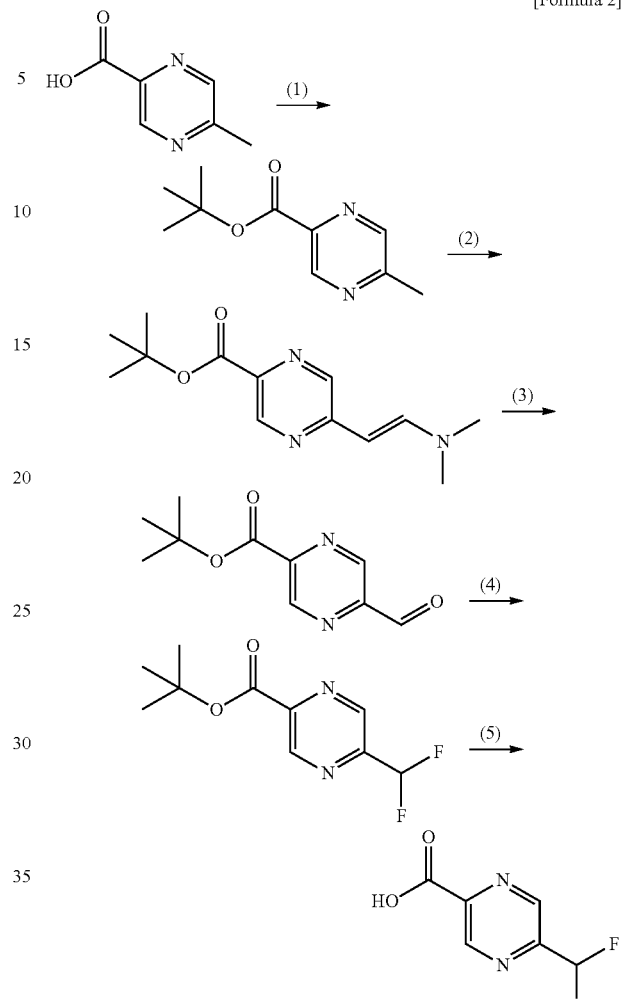

In the above formulas, R represents hydrogen, fluorine, methyl, ethyl, fluoromethyl, difluoromethyl, trifluoromethyl, methoxy, ethoxy, methoxymethyl, and the like.

The aforementioned compounds share, as a common partial structural motif, 5-(difluoromethyl)pyrazine-2-carboxamide, and these compounds are produced from the intermediate of 5-(difluoromethyl)pyrazine-2-carboxylic acid. As to the method for producing 5-(difluoromethyl)pyrazine-2-carboxylic acid (CAS Registry Number: 1174321-06-2), Production Example 17 of Patent Literature 1 describes that 5-(difluoromethyl)pyrazine-2-carboxylic acid can be produced by production steps such as ones illustrated in the following scheme using 5-methylpyrazine-2-carboxylic acid as a starting material.

CITATION LIST

Patent Literature

[Patent Literature 1] WO 2009/091016
[Patent Literature 2] U.S. Patent Publication No. 2009-0209755
[Patent Literature 3] Japanese Patent No. 4520533
[Patent Literature 4] U.S. Patent Publication No. 2010-0093999
[Patent Literature 5] WO 2010/038686
[Patent Literature 6] WO 2011/005738
[Patent Literature 7] WO 2011/009897
[Patent Literature 8] WO 2011/009898
[Patent Literature 9] WO 2011/138293

Non Patent Literature

[Non Patent Literature 1] Klein W L and seven others, Alzheimer's disease-affected brain: Presence of oligomeric Aβ ligands (ADDLs) suggests a molecular basis for reversible memory loss, Proceeding National Academy of Science USA 2003, September 2; 100 (18), pp. 10417 to 10422.
[Non Patent Literature 2] Nitsch R M and 16 others, Antibodies against β-amyloid slow cognitive decline in Alzheimer's disease, Neuron, 2003, May 22; 38, pp. 547 to 554.

[Non Patent Literature 3] Jarrett J T and two others, The carboxy terminus of the β amyloid protein is critical for the seeding of amyloid formation: Implications for the pathogenesis of Alzheimers' disease, Biochemistry, 1993, 32 (18), pp. 4693 to 4697.

[Non Patent Literature 4] Glenner G G and one other, Alzheimer's disease: initial report of the purification and characterization of a novel cerebrovascular amyloid protein, Biochemical and biophysical research communications, 1984, May 16, 120 (3), pp. 885 to 890.

[Non Patent Literature 5] Masters C L and five others, Amyloid plaque core protein in Alzheimer disease and Down syndrome, Proceeding National Academy of Science USA, 1985, June, 82 (12), pp. 4245 to 4249.

[Non Patent Literature 6] Gouras G K and 11 others, Intraneuronal Aβ42 accumulation in human brain, American Journal of Pathology, 2000, January, 156 (1), pp. 15 to 20.

[Non Patent Literature 7] Scheuner D and 20 others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2 (8), pp. 864 to 870.

[Non Patent Literature 8] Forman M S and four others, Differential effects of the Swedish mutant amyloid precursor protein on β-amyloid accumulation and secretion in neurons and nonneuronal cells, The Journal of Biological Chemistry, 1997, Dec. 19, 272 (51), pp. 32247 to 32253.

SUMMARY OF INVENTION

Technical Problem

According to the method using 5-methylpyrazine-2-carboxylic acid as a starting material illustrated in the scheme shown above as described in Production Example 17 of Patent Literature 1, deoxofluorination is necessary for the conversion of aldehyde into difluoromethyl in Step 4 (Singh, R. P.; Sheeve, J. M., Synthesis (2002) 2561: Kirk, K. L., Org. Process Res. Dev. (2008), 12, 305, and the like). As a deoxofluorinating agent, DAST: N,N-diethylamino sulfur trifluoride, Deoxo-Fluor: [bis(2-methoxyethyl)amino]sulfur trifluoride, TFEDMA: 1,1,2,2-tetrafluoro-N,N-dimethylethylamine, XtalFluor, and the like are used. These reagents can be easily purchased and are widely used for small-scale synthesis involving fluorination of a carbonyl group or hydroxyl group. However, these reagents react with water to produce deadly poisonous, glass-corrosive hydrogen fluoride; therefore, caution needs to be exercised for preparation and post-treatment of the reaction. Furthermore, these reagents are expensive and have problems associated with handling safety. As described above, from the aspects of the stability, corrosiveness, and the like of the reagents, special facilities are required for utilization of these reagents in industrial production. Furthermore, these reagents also have problems associated with the price, handling safety, and the like. In view of the above, there are still a number of problems to be solved in the conventional production method.

In light of the above, an object of the present invention is to provide an industrially advantageous method for producing 5-(difluoromethyl)pyrazine-2-carboxylic acid, which is a raw material for the construction of 5-(difluoromethyl)pyrazine-2-carboxamide, which is a common partial structural motif of the compound having an Aβ production inhibitory action or a BACE1 inhibitory action described in literatures such as Patent Literature 1.

Solution to Problem

The present invention is a method for introducing a difluoromethyl group by decarboxylating 5-[carboxy(difluoro)methyl]pyrazine-2-carboxylic acid, which is obtainable by reacting difluorobromoacetate with 5-bromopyrazine-2-carboxylate, as illustrated in the following scheme. According to this method, poisonous hydrogen fluoride is not produced in the production steps, and moreover, no special facilities are required. Furthermore, the reagents used in this reaction are inexpensive and have no problems associated with handling safety.

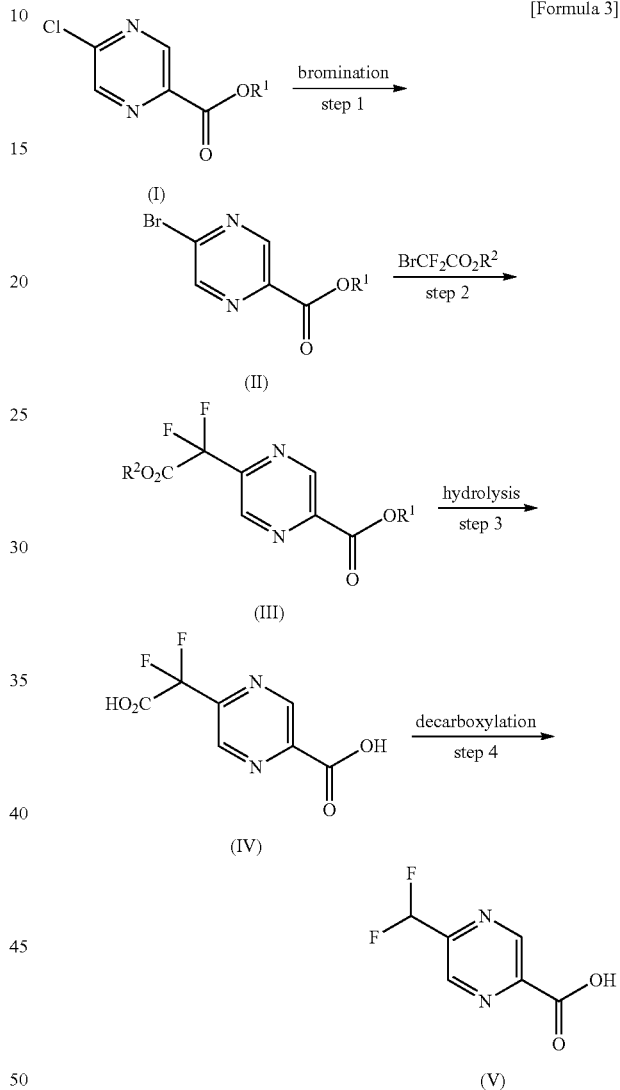

Accordingly, the present invention relates to:

[1] A method for producing 5-(difluoromethyl)pyrazine-2-carboxylic acid represented by a formula (V):

[Formula 5]

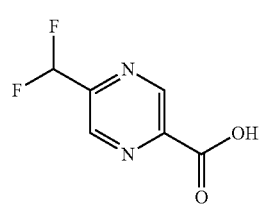

or a hydrate thereof, or a salt of 5-(difluoromethyl)pyrazine-2-carboxylic acid or a hydrate thereof, comprising a step of decarboxylating a compound represented by a formula (IV):

[Formula 4]

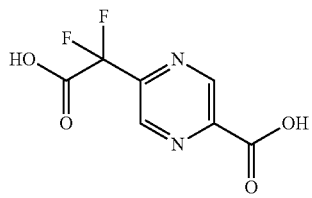
(IV)

or a salt thereof;

[2] A compound represented by a formula (IV):

[Formula 6]

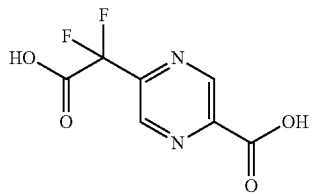
(IV)

and a salt thereof;

[3] A method for producing 5-[carboxy(difluoro)methyl]pyrazine-2-carboxylic acid represented by the following formula (IV):

[Formula 8]

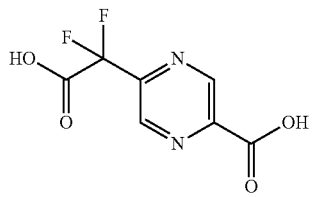
(IV)

or a salt thereof, comprising a step of hydrolyzing a compound represented by a formula (III):

[Formula 7]

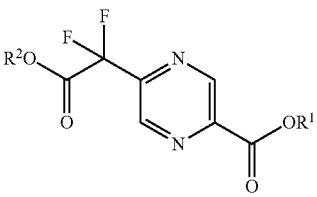
(III)

wherein $R^1$ and $R^2$ each independently represent a linear or branched $C_{1-6}$ alkyl group, or a salt thereof;

[4] The production method according to the aforementioned [3], wherein the hydrolysis is performed by using an alkali metal hydroxide;

[5] A compound represented by a formula (III):

[Formula 9]

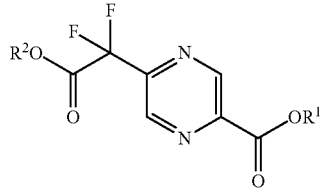
(III)

wherein $R^1$ and $R^2$ each independently represent a linear or branched $C_{1-6}$ alkyl group, or a salt thereof;

[6] A method for producing a compound represented by a formula (III):

[Formula 11]

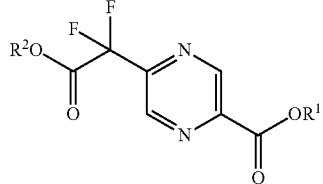
(III)

wherein $R^1$ and $R^2$ have the same meaning as defined in the aforementioned [3], or a salt thereof, comprising a step of coupling a compound represented by a formula (II):

[Formula 10]

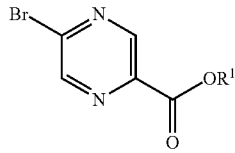
(II)

wherein $R^1$ represents a linear or branched $C_{1-6}$ alkyl group, or a salt thereof with $BrZnCF_2COOR^2$ in a presence of a copper salt;

[7] A method for producing a compound represented by the following formula (II):

[Formula 13]

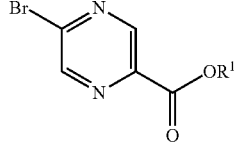
(II)

wherein $R^1$ has the same meaning as defined in the aforementioned [6], or a salt thereof, comprising a step of subjecting a compound represented by a formula (I):

[Formula 12]

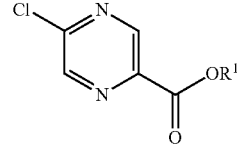
(I)

wherein R¹ has the same meaning as defined in the aforementioned [6],
or a salt thereof to a chlorine-bromine exchange reaction; and
[8] A method for producing 5-(difluoromethyl)pyrazine-2-carboxylic acid represented by a formula (V):

[Formula 18]

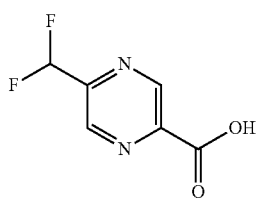

(V)

or a hydrate thereof, or a salt of 5-(difluoromethyl)pyrazine-2-carboxylic acid or a hydrate thereof, comprising steps of
i) synthesizing a compound represented by a formula (II):

[Formula 15]

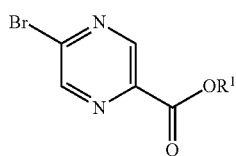

(II)

wherein R¹ has the same meaning as defined in the aforementioned [4],
or a salt thereof by subjecting a compound represented by a formula (I):

[Formula 14]

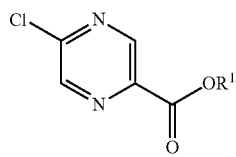

(I)

wherein R¹ has the same meaning as defined in the aforementioned [4], or a salt thereof to a chlorine-bromine exchange reaction;
ii) synthesizing a compound represented by a formula (III):

[Formula 16]

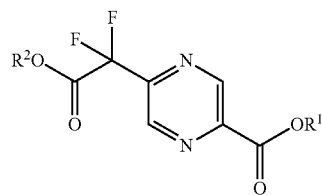

(III)

wherein R¹ and R² have the same meaning as defined in the aforementioned [3], or a salt thereof by coupling the compound represented by the formula (II) or a salt thereof with a compound represented by a formula BrZnCF₂COOR² or a salt thereof in a presence of a copper salt;
iii) subsequently, synthesizing a compound represented by a formula (IV):

[Formula 17]

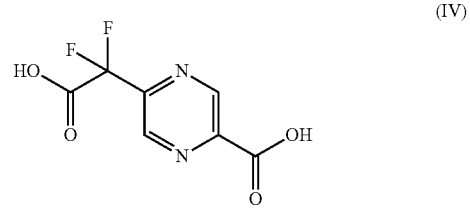

(IV)

or a salt thereof by hydrolyzing the compound represented by the formula (III) or a salt thereof; and
iv) decarboxylating the compound represented by the formula (IV) or a salt thereof.

Hereinbelow, the present invention will be described in detail with an explanation of the meaning of the symbols, terms, and the like described in the specification of the present application.

In the specification of the present application, the structural formula of the compound is not limited to the formula shown for convenience' sake but the compound may also form a salt. Further, although crystal polymorphism may exist, similarly, the compound is not limited to any crystal form but may be present in the form of any single crystal form or a mixture of multiple crystal forms, and also, the compound may be present in the form of an anhydride as well as a hydrate. All of the aforementioned forms of the compound are encompassed by the scope of the claims in the specification of the present application.

In the specification of the present application, unless otherwise specifically noted, specific examples of the salt include a hydrohalide such as hydrofluoride, hydrochloride, hydrobromide, and hydroiodide; an inorganic acid salt such as sulfate, nitrate, perchlorate, phosphate, carbonate, and bicarbonate; an organic carboxylate such as acetate, oxalate, maleate, tartrate, fumarate, and citrate; an organic sulfonate such as methanesulfonate, trifluoromethanesulfonate, ethanesulfonate, benzenesulfonate, toluenesulfonate, and camphorsulfonate; an amino acid salt such as aspartate and glutamate; a quaternary ammonium salt such as an ammonium salt, an ethyl ammonium salt, and a benzyl ammonium salt; an alkali metal salt (such as a sodium salt and a potassium salt; and an alkaline earth metal salt such as a magnesium salt and a calcium salt.

The present invention also encompasses the compounds described in the specification that are labeled with isotopes. An isotopically labeled compound is the same as the compound represented by the formula (I) except that one or more atoms are replaced by one or more atoms having an atomic mass or a mass number that is different from a commonly naturally occurring atomic mass or mass number. An isotope that can be incorporated into the compound of the present invention is an isotope of hydrogen, carbon, nitrogen, oxygen, and fluorine, which are the constituent elements of the compound, and such an isotope includes ²H, ³H, ¹¹C, ¹³C, ¹⁴C, ¹³N, ¹⁵O, ¹⁸F, and the like.

In the present specification, the term "halogen atom" refers to a fluorine atom, a chlorine atom, a bromine atom, an iodine atom, and the like, preferably a fluorine atom and a chlorine atom.

The term "linear or branched $C_{1-6}$ alkyl group" refers to an alkyl group having 1 to 6 carbon atoms, and examples of a 2-ethylbutyloxy group, a 1,3-dimethylbutyloxy group, a 2-methylpentyloxy group, and a 3-methylpentyloxy group. More preferable examples include a methoxy group, an ethoxy group, and an n-propoxy group.

The production method of the present invention is illustrated in the following reaction scheme.

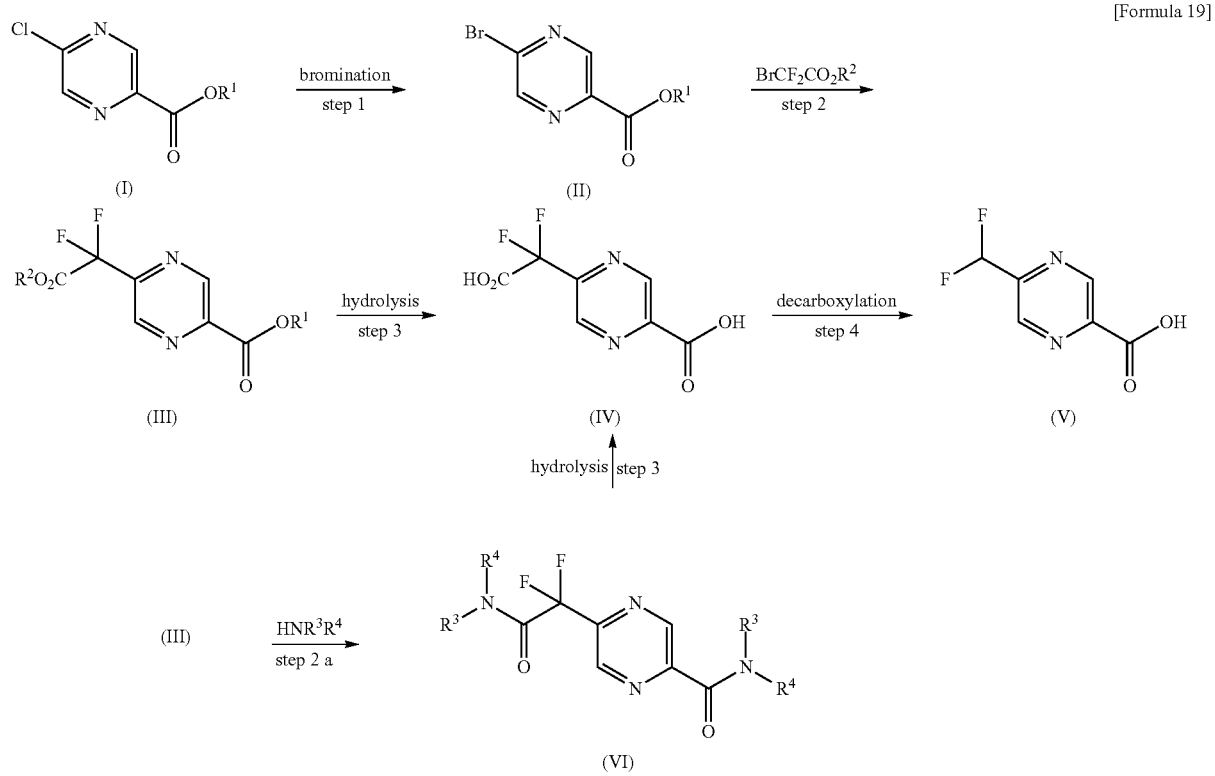

preferable group include a linear or branched $C_{1-6}$ alkyl group such as a methyl group, an ethyl group, an n-propyl group, an isopropyl group, an n-butyl group, an isobutyl group, a t-butyl group, an n-pentyl group, an isopentyl group, a neopentyl group, an n-hexyl group, a 1-methylpropyl group, a 1,2-dimethylpropyl group, a 1-ethylpropyl group, a 1-methyl-2-ethylpropyl group, a 1-ethyl-2-methylpropyl group, a 1,1,2-trimethylpropyl group, a 1-methylbutyl group, a 2-methylbutyl group, a 1,1-dimethylbutyl group, a 2,2-dimethylbutyl group, a 2-ethylbutyl group, a 1,3-dimethylbutyl group, a 2-methylpentyl group, and a 3-methylpentyl group. More preferable examples include a methyl group, an ethyl group, and an n-propyl group.

The term "linear or branched $C_{1-6}$ alkoxy group" is used to mean an oxy group bound to the aforementioned "$C_{1-6}$ alkyl group", and examples of a preferable group include a linear or branched $C_{1-6}$ alkoxy group such as a methoxy group, an ethoxy group, an n-propoxy group, an isopropoxy group, an n-butoxy group, an isobutoxy group, a t-butoxy group, an n-pentyloxy group, an isopentyloxy group, a neopentyloxy group, an n-hexyloxy group, a 1-methylpropoxy group, a 1,2-dimethylpropyloxy group, a 1-ethylpropyloxy group, a 1-methyl-2-ethylpropyloxy group, a 1-ethyl-2-methylpropyloxy group, a 1,1,2-trimethylpropyloxy group, a 1-methylbutyloxy group, a 2-methylbutyloxy group, a 1,1-dimethylbutyloxy group, a 2,2-dimethylbutyloxy group, a In the above reaction scheme, $R^1$ and $R^2$ each independently represent a linear or branched $C_{1-6}$ alkyl group, and $R^3$ and $R^4$ each independently represent a hydrogen atom, a linear or branched $C_{1-6}$ alkyl group or a benzyl group that may have a substituent such as a halogen atom, a linear or branched $C_{1-6}$ alkyl group and a linear or branched $C_{1-6}$ alkoxy group.

The production method of the present invention is a method for producing 5-(difluoromethyl)pyrazine-2-carboxylic acid (V) through multiple steps including Steps 1 to 4 using the compound (I) as a raw material.

As the compound (I), a commercially available product can be directly used. Alternatively, the compound (I) can also be produced by a method publicly known to those skilled in the art from a commercially available compound. Hereinbelow, Steps 1 to 4 will be described in detail.

Step 1:

This step is a step for obtaining the compound (II) by the chlorine-bromine exchange reaction of the compound (I).

The reaction in this step can be carried out under similar conditions to those normally used for the halogen-halogen exchange reaction of aromatic heterocyclic halogenated compounds as described in literatures (for example, T. Yajima and K. Munakata, Chem. Lett., 1977, 891).

Meanwhile, the reaction is efficiently carried out by disturbing equilibrium by continuously distilling off trimethylsilyl chloride (TMSCl) produced by the halogen-halogen exchange reaction in a method using trimethylsilyl bromide (TMSBr) described in Schlosser, M. and Cottet, F., Eur. J. Org. Chem., 2002, 4181), whereby the compound (II) can be obtained with good yield.

Specifically, the compound (I) is dissolved in an organic solvent such as acetonitrile, to which two equivalents of TMSBr is added. Reactions are allowed to proceed at 80° C. and TMSCl produced as a byproduct is distilled off under reduced pressure to disturb the equilibrium. Although no particular limitation is imposed on the reaction time, it is normally five minutes to 24 hours, preferably five minutes to 12 hours. The reaction temperature is normally room temperature to 100° C., more preferably room temperature to 80° C.

Step 2:

This step is a step for obtaining the compound (III) by coupling $BrZnCF_2COOR^2$, which is an organic zinc compound produced by reacting $BrCF_2COOR^2$ with zinc, with the compound (II).

The compound (II) used in the reaction may be one isolated in Step 1, or a reaction solution or a solution in which the solvent is replaced after post-treatment may be directly used without isolating the compound (II).

The reaction to obtain the organic zinc compound in this step can be carried out under similar conditions to those normally used for producing an organic zinc compound (the Reformatsky reagent) by reacting α-bromoacetate with zinc as described in literatures (for example, S. Reformatsky, Ber., 20, 1210 (1887), S. M. Hannick, Y. Kishi., J. Org. chem., 48, 3833 (1983), K. Tanaka, S. Kishigami, F. Toda, J. Org. Chem., 56, 4333 (1991)). The Reaction of $BrCF_2COOR^2$ with zinc can be carried out under similar conditions to those described in a literature (P. W. Konas, J. J. Pankuch, J. K. Coward, Synthesis, 2002, 2616). Further, $BrZnCF_2COOR^2$ can be stabilized in triglyme described in a literature (D. J. BURTON and J. C. EASDON, J. Fluorine Chem., 1988, 38, 125). For activation of zinc in performing the above reaction, TMSCl, TMSBr, trifluoroacetic acid, and the like are used. Although the solvent used in this reaction is not particularly limited as long as it does not interfere with the reaction, preferable examples thereof include diglyme, triglyme, toluene, xylene, 1-methyl-2-pyrrolidone, tetrahydrofuran, and 1,4-dioxane. Although no particular limitation is imposed on the reaction temperature, it is normally ice-cooling to the solvent reflux temperature, preferably, for example, 10 to 40° C. Although no particular limitation is imposed on the reaction time, it is normally 0.5 to 24 hours, preferably 0.5 to 6 hours.

The coupling reaction of $BrZnCF_2COOR^2$ with the compound (II) can be carried out under similar conditions to those described in the literature describing the use of a copper reagent (Y. Pan, C. P. Holmes, D. Tumelty, J. Org. Chem., 2005, 4897). The copper reagent used in this reaction is not particularly limited as long as it is a monovalent copper reagent, and preferable examples thereof include copper (I) bromide (CuBr). The organic zinc compound is used in an amount of one to three equivalents relative to the raw material. The copper reagent is used in an amount of one to three equivalents relative to the raw material. The solvent used in this reaction is not particularly limited as long as it does not interfere with the reaction and capable of dissolving the copper reagent, and preferable examples thereof include N,N-dimethylformamide, N,N-dimethylacetamide, 1-methyl-2-pyrrolidone, dimethyl sulfoxide, tetrahydrofuran, 1,4-dioxane, acetonitrile, and propionitrile. Although no particular limitation is imposed on the reaction temperature, it is normally ice-cooling to the solvent reflux temperature, preferably, for example, 10 to 40° C. Although no particular limitation is imposed on the reaction time, it is normally 0.5 to 24 hours, preferably 0.5 to 4 hours.

The compound (III) may undergo ester exchange during the reaction, and the compound may be present as a mixture of compounds in which $R^1$ and $R^2$ are switched.

Specifically, for example, TMSBr is added to a suspension of zinc powder in triglyme, followed by stirring at 70° C. for one hour or longer to activate the zinc powder. Then, $BrCF_2COOR^2$ is added dropwise to the suspension of zinc powder at 10 to 30° C., to which a solution of the compound (II) obtained by Step 1 in N,N-dimethylacetamide is added at 0° C. The resulting solution was warmed to 20° C. and CuBr is added in small portions. Upon completion of the reaction, the reaction solution is diluted with toluene and washed with hydrochloric acid and aqueous sodium chloride. The toluene solution thus obtained is directly used in the step 3.

Also, the reaction in this step 2 can be carried out under similar conditions to those used for reacting halopyridine or halobenzene directly with $BrCF_2COOR^2$ in the presence of copper as described in literatures such as (M. S. Ashwood et al, Tetrahedron Lett., 43 (2002) 9271, Y. Kobayashi et al., Tetrahedron Lett., 27 (1986) 6103, I. Kumadaki et al., J. Fluorine Chem., 125 (2004) 509) without using $BrZnCF_2COOR^2$. However, as will be demonstrated in Reference Example to be described later, drastic degradation was observed in the copper-catalyzed coupling of the compound (II) with $BrCF_2COOR^2$, resulting in a yield of the compound (III) of as low as about 17%, revealing that this reaction is not practical.

Step 2a:

This step is a step for obtaining the compound (VI) by reacting the compound (III) with an amine compound of $HNR^3R^4$.

The compound (III) used in the reaction may be a mixture of ester-exchanged compounds. Alternatively, it may also be an isolated compound, or a solution after post-treatment may also be directly used without isolating the compound (III).

As the reaction condition, for example, ammonia, methylamine, ethylamine, 1-propylamine or benzylamine may be used, and an organic solvent such as methanol, ethanol and isopropanol may be used if necessary. Although no particular limitation is imposed on the reaction temperature, it is normally 0° C. to the solvent reflux temperature, preferably, the room temperature to 50° C. Although no particular limitation is imposed on the reaction time, it is normally 5 minutes to 48 hours.

Step 3:

This step is a step for obtaining the compound (IV) by hydrolyzing the compound (III) or the compound (VI).

The compound (III) used in the reaction may be a mixture of ester-exchanged compounds. Alternatively, it may also be an isolated compound, or a solution after post-treatment may also be directly used without isolating the compound (III). The compound (VI) used in the reaction may be an isolated compound, or a solution after post-treatment may also be directly used without isolating the compound (VI).

As to the reaction conditions, for example, an aqueous solution of sodium hydroxide, an aqueous solution of lithium hydroxide, and an aqueous solution of potassium hydroxide can be used, and an organic solvent such as methanol and ethanol is used as needed. Although no particular limitation is imposed on the reaction temperature, it is normally 0° C. to the solvent reflux temperature, preferably room temperature to 50° C. Although no particular limitation is imposed on the reaction time, it is normally five minutes to 48 hours.

The compound (IV) may be in the free form or in the form of a salt or a hydrate. For example, when it is in the form of a salt, the salt is not particularly limited as long as it is an alkali metal salt or an organic amine salt, preferable examples thereof include a lithium salt, a potassium salt, a sodium salt, a benzylamine salt, a pyridine salt and an isopropylamine salt.

Step 4:

This step is a step for converting the compound (IV) into the compound (V) by the decarboxylation reaction. The compound (IV) used in this step may be in the free form or in the form of a salt.

The reaction in this step can also be carried out under similar conditions to those normally used for decarboxylation of carboxylic acid. Particularly, the reaction can also be carried out under similar conditions to those used for decarboxylation of 2-allyl-2,2-difluoroacetic acid described in a literature (H. Amii et al., Org. Lett., 13 (2011) 5560).

In this step, the reaction is preferably carried out under acidic conditions by directly using the compound (IV), which is an acidic compound, in the free form, or separately adding an acid. Examples of the acid to be used include phosphoric acid, hydrochloric acid, sulfuric acid, and trifluoroacetic acid.

The compound (V) may be in the free form or in the form of a salt, and when it is in the free form, it may be an anhydride or a hydrate.

Representative examples of the production method of the compound (V) are as described above. The raw material compounds and a variety of reagents in the production method of the compound (V) may form a salt or a hydrate, and they vary depending on the starting materials, solvents used, and the like, and are not particularly limited as long as they do not interfere with the reaction. Solvents used also vary depending on the starting materials, reagents, and the like, and needless to say, they are not particularly limited as long as they do not interfere with the reaction and can dissolve a certain amount of starting materials. When the compound (V) is obtained in the free form, the compound (V) can be converted into the state of a salt that can be formed by the compound (V) as described above according to a routine method. Similarly, when the compound (V) is obtained as a salt of the compound (V), it can be converted into the free form of the compound (V) according to a routine method.

Hereinbelow, the present invention will be described in detail with reference to Examples and Reference Example; however, the present invention is not limited thereto. Also, the abbreviations used in Examples are conventional abbreviations well-known to those skilled in the art, some of which are shown below.

DMA; N,N-dimethylacetamide
DMF; N,N-dimethylformamide
TFA; trifluoroacetic acid
NMP; 1-methyl-2-pyrrolidone
TMSCl; trimethylsilyl chloride
TMSBr; trimethylsilyl bromide
Copper (I) bromide; CuBr The chemical shift in the proton nuclear magnetic resonance spectrum is recorded in the δ unit relative to tetramethylsilane (ppm), and the coupling constant is recorded in hertz (Hz). The patterns are: s; singlet, d; doublet, t; triplet, q; quartet, and br; broad.

HPLC: Shimadzu Corporation, Prominence (R)
NMR: JEOL Ltd., JNM-AL400-type nuclear magnetic resonance apparatus (400 MHz)

Hereinbelow, the "room temperature" in Examples and Reference Example normally refers to about 10° C. to about 35° C. Unless otherwise specifically noted, % indicates weight percent.

EXAMPLE 1

Preparation of 5-(difluoromethyl pyrazine-2-carboxylic acid (V)

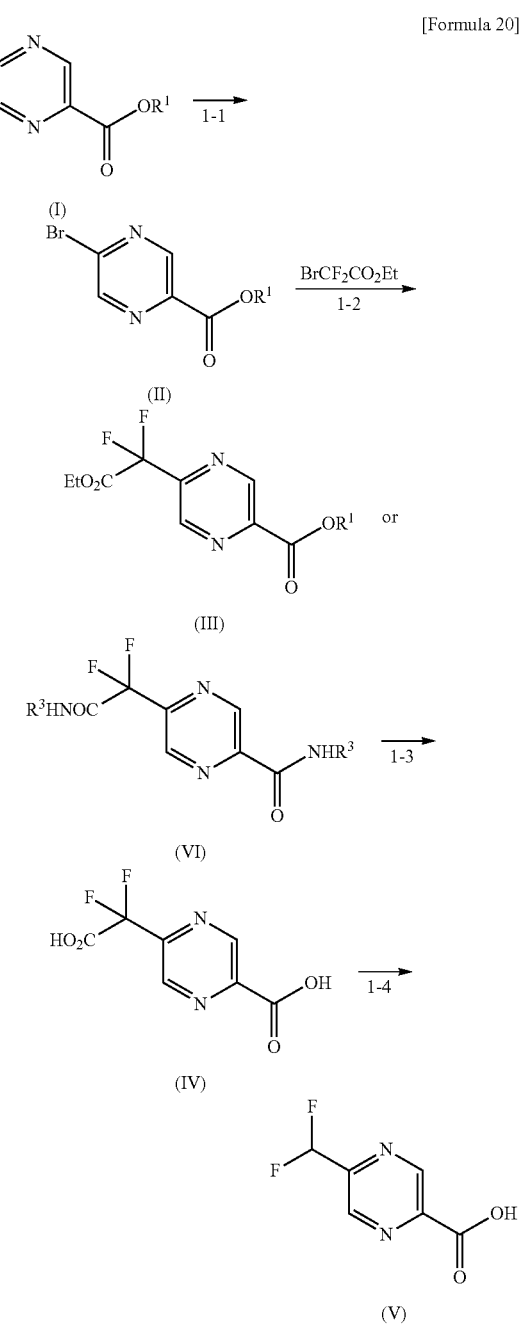

[Formula 20]

In the above reaction scheme, $R^1$ is a methyl group, an ethyl group or an isopropyl group, and $R^3$ is a methyl group.

(1-1) Preparation of methyl 5-bromopyrazine-2-carboxylate (II)

(1-1)-A

To a solution of methyl 5-chloropyrazine-2-carboxylate (I, 138.0 g, 0.800 mol) in acetonitrile (690 mL) was added TMSBr (207.6 mL, 1.600 mol) under nitrogen atmosphere, and the resulting mixture was stirred at 80° C. for 20 min. After about 138 mL of volatile component was removed by distillation under reduced pressure (atmospheric pressure to 940 hPa), acetonitrile (138 mL) was added to the mixture and 138 mL of volatile component was redistilled away under reduced pressure (atmospheric pressure to 875 hPa) at 80° C. After the reaction was cooled to around room temperature, an aqueous sodium bicarbonate solution (6.3%, 1104 g) and ethyl acetate (340 mL) were added to the reaction. After phase separation of the mixture, the aqueous layer was re-extracted with ethyl acetate (690 mL). The organic layers were combined and washed with aqueous sodium chloride solution (5%, 363 g). The organic layer was concentrated at 60° C. under reduced pressure, and DMA was added to the residue and the mixture was concentrated again at 60° C. under reduced pressure to afford 1827.0 g of a DMA solution of the title compound (II) (title compound (II), 145.3 g, 84% yield). Content of the title compound (II) was determined by HPLC and the ratio of I and II were shown as 3.9:96.1 by HPLC analysis.

The data of $^1$H NMR of the title compound is as follows:
$^1$H NMR (400 MHz, DMSO-$d_6$) δ: 3.91 (s, 3H), 9.01 (s, 3H), 9.01 (m, 2H).

HPLC was performed under the following conditions.
HPLC Parameters:

| HPLC column: | Sunniest RP-AQUA, 4.6 × 150 mm | | |
|---|---|---|---|
| Temperature: | 45° C. | | |
| Flow rate: | 1 mL/min. | | |
| Mobile phase (Solvent A) | Acetonitrile/water/TFA = 10 mL/990 mL/1 mL | | |
| Mobile phase (Solvent B) | Acetonitrile/water/TFA = 900 mL/100 mL/1 mL | | |
| Gradient: | Time, min | %-Solvent A | %-Solvent B |
| | Initial | 100 | 0 |
| | 30 | 70 | 30 |
| | 35 | 0 | 100 |
| | 45 | 0 | 100 |
| | 45.01 | 100 | 0 |
| | 55 | 100 | 0 |
| Detection: | 270 nm UV | | |
| Run time: | 55 min | | |
| I Retention time: | 17.8 min | | |
| II Retention time: | 20.0 min | | |

(1-1)-B

To a solution of methyl 5-chloropyrazine-2-carboxylate (I, 30.0 g, 0.174 mol) in acetonitrile (120 mL) TMSBr (45.1 mL, 0.348 mol) was added under nitrogen atmosphere. The mixture was stirred and heated at 80° C. for 5 h while volatile component (105 mL) was distilled away under reduced pressure (atmospheric pressure to 800 hPa). After the mixture was cooled to 0° C., water (150 mL) was added while keeping the internal temperature at 0 to 8° C., and the mixture was stirred at 0° C. for 1 h. The precipitated solids were collected by filtration, washed with water (120 mL), and dried under reduced pressure at 50° C. to provide 35.0 g of the title compound (II) (93% yield) as brown solids. The ratio of I and II was 1.1:98.9 by its HPLC analysis.

(1-2) Preparation of methyl 5-(2-ethoxy-1,1-difluoro-2-oxoethyl)pyrazine-2-carboxylate (III)

To the mixture of zinc powder (46.0 g, 0.703 mol) and triglyme (352 mL) was added TMSBr (9.12 mL, 0.070 mol) under nitrogen, and the mixture was stirred at 70° C. for 1.5 h. After the mixture was cooled to room temperature, ethyl bromodifluoroacetate (108.6 mL, 0.847 mol) was added while keeping the internal temperature at 18 to 31° C., and the mixture was stirred at 20° C. for 30 min and then cooled to 10° C. After a DMA solution of methyl 5-bromopyrazine-2-carboxylate (II, gross 914 g, net 72.7 g, 0.335 mol) was added to the mixture and rinsed the vessel with DMA (166 mL), the mixture was warmed to 20° C. Copper bromide (CuBr, 100.9 g, 0.703 mol) was added in fifth portions over 1 h, followed by stirring the mixture for 30 min. The reaction mixture was transferred into a pre-cooled (10° C.) mixture of an aqueous sodium chloride solution (10%, 705 g), hydrochloric acid (5 M, 705 mL) and toluene (1409 mL), and the resulting mixture was vigorously stirred. After phase separation, the organic layer was washed twice with aqueous sodium chloride solution (5.7%, 705 g and 2.9%, 705 g) to afford 1378 g of a toluene solution of the title compound (III). Compound (III) was obtained as a mixture of four derivatives of methyl and ethyl esters, and directly used as 100% yield to the next step.

The data of $^1$H NMR for each ester compound is as follows:

Methyl 5-(1,1-difluoro-2-methoxy-2-oxoethyl)pyrazine-2-carboxylate $^1$H NMR (400 MHz, DMSO-$d_6$) δ: 3.88 (s, 3H), 3.95 (s, 3H), 9.29 (m, 2H).

Methyl 5-(2-ethoxy-1,1-difluoro-2-oxoethyl)pyrazine-2-carboxylate $^1$H NMR (400 MHz, DMSO-$d_6$) δ: 1.22 (t, J=7.2 Hz, 2H), 3.95 (s, 3H), 4.34 (q, J=7.2 Hz, 2H), 9.29 (m, 2H).

Methyl (5-ethoxycarbonylpyrazin-2-yl)-difluoroacetate $^1$H NMR (400 MHz, DMSO-$d_6$) δ: 1.35 (t, J=7.2 Hz, 3H), 3.88 (s, 3H), 4.41 (q, J=7.2 Hz, 2H), 9.29 (m, 2H).

Ethyl 5-(2-ethoxy-1,1-difluoro-2-oxoethyl)pyrazine-2-carboxylate $^1$H NMR (400 MHz, DMSO-$d_6$) δ: 1.22 (t, J=7.2 Hz, 2H), 1.35 (t, J=7.2 Hz, 3H), 4.34 (q, J=7.2 Hz, 2H), 4.41 (q, J=7.2 Hz, 2H), 9.29 (m, 2H).

1-3)-A Preparation of benzyl amine salt of 5-[carboxy(difluoro)methyl]pyrazine-2-carboxylic acid (IV)

To a toluene solution of methyl 5-(2-ethoxy-1,1-difluoro-2-oxoethyl)pyrazine-2-carboxylate (III, gross 1378 g, 0.335 mol as 100% yield at former step, example (1-2)) was added an aqueous sodium hydroxide solution (5 M, 268 mL, 1.34 mol), and the mixture was stirred at room temperature for 15 h. After addition of concentrated hydrochloric acid (32 mL) was to the mixture and phase separation, the organic layer was re-extracted with water (44 mL). The aqueous layers were combined, and then isopropyl acetate (732 mL) and conc. hydrochloric acid (32 mL) were added. After phase separation, the aqueous layer was re-extracted with isopropyl acetate (366 mL). After the organic layers were combined, 2-propanol (1098 mL) was added followed by addition of benzylamine (109.7 mL, 1.00 mol) while maintaining the internal temperature at 16 to 20° C., and the suspension was stirred at room temperature for 2 h. The precipitated solids were collected by filtration, washed with 2-propanol (174 mL), and dried at 60° C. under reduced pressure to provide 115.6 g of the title compound (dibenzylamine salt of IV, 80% yield based on methyl ester (II)) as pale brown solids.

The data of $^1$H NMR of the title compound is as follows.
$^1$H NMR (400 MHz, DMSO-$d_6$) δ: 4.02 (s, 4H), 7.38 (m, 10H), 8.72 (s, 1H), 8.98 (s, 1H).

(1-3)-B Preparation of potassium salt of 5-[carboxy(difluoro)methyl]pyrazine-2-carboxylic acid (IV)

To a mixture of zinc powder (4.58 g, 0.070 mol) and triglyme (35 mL) was added TMSBr (0.91 mL, 0.007 mol) under nitrogen, and the mixture was stirred at 70° C. for 1.5 h. After the mixture was cooled to room temperature, ethyl bromodifluoroacetate (10.8 mL, 0.084 mol) was added while maintaining the internal temperature at 22 to 27° C., and the mixture was stirred at 20° C. for 30 min and then cooled to 0° C. After addition of methyl 5-bromopyrazine-2-carboxylate (II, 7.23 g, 0.033 mol) in DMA (106 mL) to the mixture, the resulting mixture was warmed to 20° C. Copper bromide (CuBr, 10.0 g, 0.070 mol) was added in fifth portions over 1 h followed by stirring the mixture for 30 min. The reaction mixture was transferred into a pre-cooled (ice bath) mixture of an aqueous sodium chloride solution (6.3%, 111 g), concentrated hydrochloric acid (29.4 mL) and toluene (140 mL), and the resulting mixture was vigorously stirred. The organic layer was separated and washed twice with aqueous sodium chloride solutions (5.7%, 70 g and 2.9%, 70 g) to afford 136 g of a toluene solution of methyl 5-(2-ethoxy-1,1-difluoro-2-oxoethyl)pyrazine-2-carboxylate (III).

To the obtained toluene solution of methyl 5-(2-ethoxy-1,1-difluoro-2-oxoethyl)pyrazine-2-carboxylate (III, gross 34.0 g, 8.33 mmol as 100% yield) were added water (3 mL) and an aqueous potassium hydroxide solution (48%, 4.87 g, 41.7 mmol), and the mixture was stirred at room temperature for 14 h. After phase separation, the organic layer was re-extracted with water (1 mL). After combining the obtained two aqueous layers, methanol (20 mL) was added to the aqueous layer, and the resulting suspension was stirred for 1 h while ice cooling. The precipitated solids were collected by filtration, washed with methanol (5 mL), and dried at 50° C. under reduced pressure to afford 1.83 g of the title compound (potassium salt of IV) as ocher solids. Water content of the obtained title compound was 5.93%, and the content as a free form was determined as 72.5% based on a calibration curve prepared by HPLC (chemical yield was 73% from the methyl ester (II)).

The data of $^1$H NMR is as follows.
$^1$H NMR (400 MHz, DMSO-$d_6$) δ: 8.63 (d, J=1.6 Hz, 1H), 8.90 (d, J=1.6 Hz, 1H).

The water content was measured by Karl Fischer titration. The same parameters for HPLC (retention time of IV was 7.0 min) as described in example (1-1) were applied.

(1-3)-C Preparation of potassium salt of 5-[carboxy(difluoro)methyl]pyrazine-2-carboxylic acid (IV)

To a mixture of zinc powder (2.29 g, 0.035 mol) and triglyme (17.5 mL) was added TMSBr (0.45 mL, 0.004 mol) under nitrogen, and the mixture was stirred at 70° C. for 1.5 h. After the reaction mixture was cooled to room temperature, ethyl bromodifluoroacetate (5.41 mL, 0.042 mol) was added while maintaining the internal temperature at 22 to 27° C., and the mixture was stirred at 20° C. for 30 min and then cooled to 0° C. After addition of a solution of isopropyl 5-bromopyrazine-2-carboxylate (II, 4.48 g, 0.017 mol) in DMA (51 mL) to the reaction mixture, the resulting mixture was warmed to 20° C. Copper bromide (CuBr, 5.02 g, 0.035 mol) was added in fifth portions over 1 h followed by stirring the mixture for 30 min. The resulting mixture was transferred into a pre-cooled (ice bath) mixture of an aqueous sodium chloride solution (6.3%, 55.5 g), concentrated hydrochloric acid (14.7 mL) and toluene (70 mL), and the resulting mixture was vigorously stirred. After phase separation, the organic layer was washed twice with an aqueous sodium chloride solution (5.7%, 35 g and 2.9%, 35 g) to afford 74.2 g of a toluene solution of isopropyl 5-(2-ethoxy-1,1-difluoro-2-oxoethyl)pyrazine-2-carboxylate (III).

To the obtained toluene solution of isopropyl 5-(2-ethoxy-1,1-difluoro-2-oxoethyl)pyrazine-2-carboxylate (III, gross 37.1 g, 8.33 mmol as 100% yield) were added water (3 mL) and an aqueous potassium hydroxide solution (48%, 4.87 g, 41.7 mmol), and the mixture was stirred at room temperature for 14 h. After extraction with water (1 mL), the organic layer was re-extracted with water (1 mL). After combining the obtained two aqueous layers, methanol (25 mL) was added, and the suspension was stirred for 1 h while ice cooling. The precipitated solids were collected by filtration, washed with methanol (5 mL), and dried at 50° C. under reduced pressure to afford 1.99 g of the title compound (potassium salt of IV) as ocher solids. The water content of the obtained title compound (potassium salt of IV) was 5.96%, and the content as a free form was determined as 70.8% a calibration curve prepared by HPLC (chemical yield was 78% from the isopropyl ester (II)).

(1-3)-D Preparation of 5-[1,1-difluoro-2-(methylamino)-2-oxoethyl]-N-methylpyrazine-2-carboxamide (VI)

To the toluene solution of methyl 5-(2-ethoxy-1,1-difluoro-2-oxoethyl)pyrazine-2-carboxylate (III, gross 6.80 g, 1.67 mmol as 100% yield) which was obtained from example (1-3)-B was added a methanol solution of methylamine (9.8 M, 0.52 mL, 5.0 mmol), and the mixture was stirred at room temperature for 45 h. To the reaction mixture were added methanol solution of methylamine (9.8 M, 0.52 mL, 5.0 mmol) and 2-propanol (1 mL), and the resulting mixture was stirred for 24 h. After addition of water (2 mL) and stirring the suspension for 3.5 h while ice-cooling, the precipitated solids were collected by filtration and washed with toluene (0.5 mL) and water (0.5 mL), respectively. The obtained solids were dried at room temperature under reduced pressure to afford the title compound (VI, 224 mg, 55% yield) as white solids.

The data of $^1$H NMR of the obtained title compound is as follows.
$^1$H NMR (400 MHz, DMSO-$d_6$) δ: 2.70 (d, J=4.8 Hz, 3H), 2.83 (d, J=4.8 Hz, 3H), 9.02-9.09 (m, 2H), 9.05 (m, 1H), 9.24 (m, 1H).

(1-4)-A Preparation of 5-(difluoromethyl)pyrazine-2-carboxylic acid (V)

To a mixture of benzyl amine salt of 5-[carboxy(difluoro)methyl]pyrazine-2-carboxylic acid (IV, 110 g, 0.245 mol) and water (460 mL) were added toluene (550 mL) and an aqueous sodium hydroxide solution (5 M, 127 mL), and the aqueous layer was separated. After addition of phosphoric acid (85%, 121 mL, 1.78 mol) to the obtained aqueous layer and stirring the mixture at 110° C. for 24 h, and the reaction was cooled to room temperature. An aqueous sodium hydroxide solution (48%, 140 mL) was added, and the resulting mixture was stirred at 110° C. for 22 h and then cooled to room temperature. After addition of isopropyl acetate (412 mL) and concentrated hydrochloric acid (210 mL), the mixture was passed through a filter and the filter was rinsed with isopropyl acetate (137 mL). After phase separation of the obtained mixture, the aqueous layer was re-extracted with isopropyl acetate (550 mL). The obtained two organic layers were combined and washed six times with water (165 mL each), and the six washings were combined and re-extracted with isopropyl acetate (550 mL). After combining the obtained two organic layers, concentration at 50° C. under reduced pressure, and cooling the residue (about 93 mL) to 20° C. followed by addition of n-heptane (155 mL) over 1 h, the mixture was cooled to −10° C. The precipitated solids were collected by filtration, washed with n-heptane (53 mL), and dried at 50° C. under reduced pressure to afford the title compound (V, 29.1 g, 66% yield) as yellow solids.

The data of $^1$H NMR for the title compound (V) is as follows.

$^1$H NMR (400 MHz, DMSO-$d_6$) δ: 7.20 (t, J=54 Hz, 1H), 9.07 (s, 1H), 9.27 (s, 1H), 14.0 (br, 1H).

(1-4)-B Preparation of 5-(difluoromethyl)pyrazine-2-carboxylic acid (V)

To a mixture of wet solids (235 g including 2-propanol) of benzyl amine salt of 5-[carboxy(difluoro)methyl]pyrazine-2-carboxylic acid (IV, 214 g, 0.495 mol,) and toluene (1070 mL) were added water (303 mL) and an aqueous sodium hydroxide solution (48%, 68.3 mL), and the aqueous layer was separated. After the organic layer was re-extracted with water (107 mL), the aqueous layers were combined. To the aqueous layer were added cyclopentyl methyl ether (2141 mL) and concentrated hydrochloric acid (165 mL), and the organic layer was separated.

The aqueous layer was re-extracted with cyclopentyl methyl ether (963 mL), and the vessel rinsed with cyclopentyl methyl ether (107 mL) followed by combining the obtained three organic layers. After the mixture was stirred at 90° C. for 30 h and cooled to room temperature, water (828 mL) and sodium hydroxide solution (48%, 54.6 mL) were added to the mixture. After phase separation, the organic layer was re-extracted with water (107 mL), and the obtained two aqueous layers were combined. Phase separation was conducted after addition of isopropyl acetate (2141 mL) and concentrated hydrochloric acid (86.6 mL), and the aqueous layer was re-extracted with isopropyl acetate (1070 mL). After combining the obtained two organic layers, the organic layers were washed with water (321 mL). Insoluble materials in the organic layer was removed by polish filtration through and the filter was rinsed with isopropyl acetate (107 mL). The obtained organic layer was concentrated at 50° C. under reduced pressure, and the residue (about 188 mL) was diluted with isopropyl acetate (46 mL) followed by cooling to 30° C. After addition of n-heptane (640 mL) over 1 h, the mixture was cooled to −10° C. The precipitated solids were collected by filtration, washed with n-heptane (117 mL), and dried at 50° C. under reduced pressure to afford the title compound (V, 68.2 g, 79% yield) as flesh colored solids.

(1-4)-C Preparation of 5-(difluoromethyl)pyrazine-2-carboxylic acid (V)

To a mixture of potassium salt of 5-[carboxy(difluoro)methyl]pyrazine-2-carboxylic acid (IV, 1.00 g, 3.32 mmol) which was obtained from example (1-3)-B, isopropyl acetate (4 mL), and water (2 mL) were added concentrated sulfuric acid (0.60 mL, 10.8 mmol), and the organic layer was separated. The aqueous layer was re-extracted with isopropyl acetate (4 mL) followed by combining the obtained two organic layers. After stirring the mixture at 75° C. for 16.5 h, the mixture was stirred at 80° C. for 6 h and cooled to room temperature. After polish filtration of the mixture through a filter and rising the filter with isopropyl acetate (1 mL), water (4 mL) and aqueous sodium hydroxide solution (48%, 973 mg, 8.33 mmol) were added to the filtrate, and then the aqueous layer was separated. To the aqueous layer was added concentrated hydrochloric acid (0.83 mL, 10.0 mmol), and the resulting mixture was stirred while in ice-cooling for 17 h. The precipitated solids were collected by filtration, washed with water (0.5 mL), and dried at 50° C. under reduced pressure to afford the title compound (V, 371 mg, 64% yield) as pale brown solids.

(1-4)-D Preparation of potassium salt of 5-(difluoromethyl)pyrazine-2-carboxylic acid (V)

To a mixture of potassium salt of 5-[carboxy(difluoro)methyl]pyrazine-2-carboxylic acid (IV, 1.00 g, 3.24 mmol) which was obtained from example (1-3)-C, isopropyl acetate (4 mL), and water (2 mL) was added concentrated sulfuric acid (0.60 mL, 10.8 mmol), and the organic layer was separated. The aqueous layer was re-extracted with isopropyl acetate (4 mL) followed by combining the two organic layers. After stirring the obtained isopropyl acetate solution mixture at 75° C. for 16.5 h, and the solution was stirred at 80° C. for 6 h followed by cooling to room temperature. The reaction mixture was passed through a filter, and the filter was rinsed with isopropyl acetate (1 mL). To the filtrate were added methanol (4 mL) and an aqueous potassium hydroxide solution (48%, 973 mg, 8.33 mmol) followed by stirring the mixture while ice-cooling for 17 h. The precipitated solids were collected by filtration, washed with isopropyl acetate (1 mL), and dried at 50° C. under reduced pressure to afford the title compound (potassium salt of V, 433 mg, 63% yield) as pale brown solids.

The data of $^1$H NMR for the title compound is as follows.

$^1$H NMR (400 MHz, DMSO-$d_6$) δ: 7.07 (t, J=54 Hz, 1H), 8.76 (s, 1H), 8.97 (s, 1H).

Reference Example

[Formula 21]

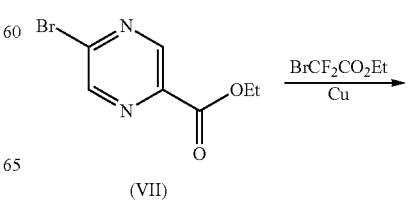

23
-continued

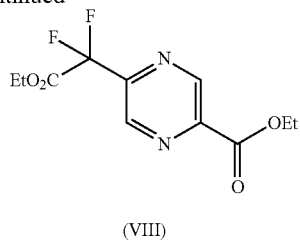

(VIII)

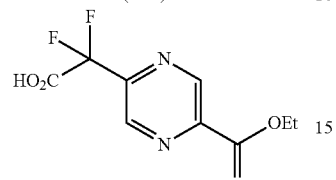

(IX)

Preparation of the mixture of ethyl 5-(2-ethoxy-1,1-difluoro-2-oxoethyl)pyrazine-2-carboxylate (VIII) and [5-(ethoxycarbonyl)pyrazin-2-yl](difluoro)acetic acid (IX)

To a mixture of copper powder (286 mg, 4.50 mmol) and DMF (3.5 mL) was added TFA (11 μL, 0.15 mmol), and the resulting mixture was stirred at room temperature for 30 min. To the mixture were added ethyl 5-bromopyrazine-2-carboxylate (VII, 347 mg, 1.50 mmol) and ethyl bromodifluoroacetate (289 μL, 2.25 mmol), and the mixture was stirred at 50° C. for 2 h. To the reaction mixture were added a saturated aqueous sodium bicarbonate solution (10 mL) and ethyl acetate (15 mL), and the organic layer was separated. The organic layers was washed twice with an aqueous sodium chloride solution (5%, 20 mL each). After the organic layer was dried over sodium sulfate, concentration at 40° C. under reduced pressure and purification of the residue by silica gel chromatography (ethyl acetate and n-hexane) afforded the title compound (VIII, 30.9 mg, 8% yield and IX, 34.9 mg, 9% yield).

The data of $^1$H NMR for the title compound (IX) is as follows.

[5-(ethoxycarbonyl)pyrazin-2-yl](difluoro)acetic acid (IX)

$^1$H NMR (400 MHz, CDCl$_3$) δ: 1.49 (t, J=6.8 Hz, 3H), 4.55 (q, J=6.8 Hz, 2H), 9.40 (s, 1H), 9.76 (s, 1H).

24

INDUSTRIAL APPLICABILITY

According to the production method of the present invention, 5-(difluoromethyl)pyrazine-2-carboxylic acid, which is a raw material for the construction of 5-(difluoromethyl)pyrazine-2-carboxamide, which is a common partial structural motif of the compound having an Aβ production inhibitory action or a BACE1 inhibitory action, can be industrially advantageously produced.

The invention claimed is:

1. A method for producing 5-(difluoromethyl)pyrazine-2-carboxylic acid represented by a formula (V):

[Formula 2]

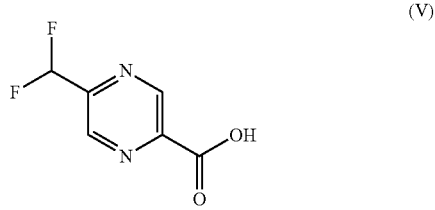

(V)

or a hydrate thereof, or a salt of 5-(difluoromethyl)pyrazine-2-carboxylic acid or a hydrate thereof, comprising a step of decarboxylating a compound represented by a formula (IV):

[Formula 1]

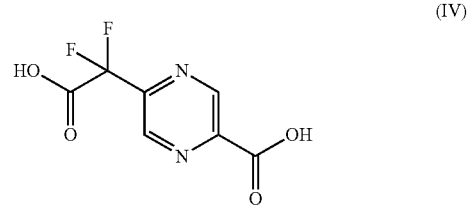

(IV)

or a salt thereof.

* * * * *